US006846801B1

(12) United States Patent
Bäckström et al.

(10) Patent No.: US 6,846,801 B1
(45) Date of Patent: *Jan. 25, 2005

(54) SYSTEMIC ADMINISTRATION OF A THERAPEUTIC PREPARATION

(75) Inventors: Kjell Göran Erik Bäckström, Lund (SE); Carl Magnus Olof Dahlbäck, Lund (SE); Peter Edman, Bjärred (SE); Ann Charlotte Birgit Johansson, Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/158,554

(22) Filed: Sep. 22, 1998

Related U.S. Application Data

(63) Continuation of application No. 08/582,702, filed on Jan. 4, 1996, now Pat. No. 5,830,853, which is a continuation-in-part of application No. 08/265,371, filed on Jun. 23, 1994, now Pat. No. 5,506,203.

(30) Foreign Application Priority Data

Jun. 24, 1993 (SE) ............................................. 9302198
Feb. 4, 1994 (SE) ............................................. 9400372

(51) Int. Cl.$^7$ ........................ A61K 38/28; C07K 14/62
(52) U.S. Cl. ............................. 514/3; 514/4; 530/303; 424/45; 424/46; 424/489
(58) Field of Search ..................... 514/3, 4; 530/303; 424/489, 45, 46

(56) References Cited

U.S. PATENT DOCUMENTS

| | | | |
|---|---|---|---|
| 2,992,645 A | 7/1961 | Fowler ................. 128/203.15 |
| 3,014,844 A | 12/1961 | Thiel ........................... 167/82 |
| 3,671,625 A | 6/1972 | Altounyan ................. 424/45 |
| 4,232,002 A | 11/1980 | Nogrady ..................... 424/45 |
| 4,462,983 A | 7/1984 | Azria et al. ................... 424/45 |
| 4,524,769 A | 6/1985 | Wetterlin ............... 128/203.15 |
| 4,534,345 A | 8/1985 | Wetterlin ............... 128/203.15 |
| 4,537,772 A | 8/1985 | Alexander et al. ............. 514/9 |
| 4,548,922 A | 10/1985 | Carey et al. ................... 514/4 |
| 4,613,500 A | 9/1986 | Suzuki et al. ............... 424/85.4 |
| 4,668,218 A | 5/1987 | Virtanen ....................... 604/58 |
| 4,690,952 A | 9/1987 | Kagatani et al. .............. 514/11 |
| 4,731,360 A | 3/1988 | Alexander et al. .......... 514/201 |
| 4,746,508 A | 5/1988 | Carey et al. ................... 424/88 |
| 4,788,221 A | 11/1988 | Kagatani et al. .............. 514/12 |
| 4,847,298 A | 7/1989 | Alexander et al. .......... 514/565 |
| 4,895,719 A | 1/1990 | Radhakrishnan ............. 424/45 |
| 4,900,730 A | 2/1990 | Miyauchi ..................... 514/12 |
| 4,907,583 A | 3/1990 | Wetterlin et al. ...... 128/203.15 |
| 4,926,852 A | 5/1990 | Zoltan et al. .......... 128/200.23 |
| 4,959,358 A | 9/1990 | Carey et al. ................ 514/171 |
| 4,963,367 A | 10/1990 | Ecanow ....................... 424/485 |
| 4,994,439 A | * 2/1991 | Longenecker et al. ......... 514/3 |
| 5,006,343 A | 4/1991 | Benson et al. |
| 5,011,678 A | 4/1991 | Wang ........................... 424/45 |
| 5,118,494 A | 6/1992 | Schultz ........................ 424/45 |
| 5,122,127 A | 6/1992 | Stanley ..................... 604/890.1 |
| 5,122,376 A | 6/1992 | Aliverti ...................... 424/405 |
| 5,179,079 A | 1/1993 | Hansen et al. ................. 514/4 |
| 5,192,548 A | 3/1993 | Velasquez et al. ........... 424/443 |
| 5,200,393 A | 4/1993 | Weiner ........................... 514/3 |
| 5,202,129 A | 4/1993 | Samejima et al. ........... 424/489 |
| 5,254,330 A | 10/1993 | Ganderton et al. ............ 424/46 |
| 5,260,306 A | 11/1993 | Boardman et al. ........... 514/291 |
| 5,284,656 A | 2/1994 | Platz et al. ................... 424/435 |
| 5,288,498 A | 2/1994 | Stanley et al. ............... 424/440 |
| 5,320,094 A | 6/1994 | Laube et al. ............ 128/203.12 |
| 5,341,800 A | 8/1994 | Clark et al. ............. 128/203.15 |
| 5,348,730 A | 9/1994 | Greenleaf ..................... 424/45 |
| 5,349,947 A | 9/1994 | Newhouse et al. ............ 424/45 |
| 5,352,461 A | 10/1994 | Feldstein et al. ............ 424/493 |
| 5,354,562 A | 10/1994 | Platz et al. ................... 424/489 |
| 5,364,838 A | 11/1994 | Rubsamen ..................... 514/3 |
| 5,376,359 A | 12/1994 | Johnson ......................... 514/3 |
| 5,376,386 A | 12/1994 | Ganderton et al. .......... 424/499 |
| 5,384,133 A | 1/1995 | Boyes et al. .................. 424/501 |
| 5,419,315 A | 5/1995 | Rubsamen .............. 128/200.14 |
| 5,437,271 A | 8/1995 | Backstrom et al. ..... 128/203.15 |
| 5,451,569 A | 9/1995 | Wong et al. .................... 514/3 |
| 5,458,135 A | 10/1995 | Patton et al. ........... 128/200.14 |
| 5,474,759 A | 12/1995 | Fassberg et al. .............. 424/45 |
| 5,482,032 A | 1/1996 | Smith et al. ............ 128/203.15 |
| 5,482,706 A | 1/1996 | Igari et al. .................. 424/85.7 |
| 5,506,203 A | * 4/1996 | Backstrom et al. ............ 514/4 |
| 5,514,670 A | 5/1996 | Friedman et al. ............... 514/2 |
| 5,518,998 A | * 5/1996 | Backstrom et al. ............ 514/3 |
| 5,607,915 A | 3/1997 | Patton ........................... 514/12 |
| 5,658,878 A | * 8/1997 | Backstrom et al. ............ 514/3 |
| 5,661,130 A | 8/1997 | Meezan et al. ................ 514/25 |
| 5,707,644 A | 1/1998 | Illum ........................... 424/434 |

(List continued on next page.)

FOREIGN PATENT DOCUMENTS

| | | |
|---|---|---|
| AU | 43356/93 | 1/1994 |
| DD | 261 096 A1 | 10/1988 |
| EP | 0 023 359 A2 | 2/1981 |
| EP | 0 055 041 | 3/1981 |
| EP | 0 122 036 | 10/1984 |

(List continued on next page.)

OTHER PUBLICATIONS

Bjork, Erik, 'Starch Microspheres as a Nasal Delievery System for Drugs', Comphrehensive summaries of Uppsala Dissertations from the Faculty of Phamacy, 103, 1993.*

(List continued on next page.)

*Primary Examiner*—Brenda Brumback
*Assistant Examiner*—Anish Gupta
(74) *Attorney, Agent, or Firm*—Fish & Richardson P.C.

(57) ABSTRACT

A method of treating a patient in need of insulin treatment, including the steps of introducing into the lower respiratory tract of the patient an effective amount of a therapeutic preparation in the form of a dry powder containing (a) insulin and (b) an enhancer compound which enhances the absorption of insulin in the lungs of the patient.

37 Claims, 7 Drawing Sheets

U.S. PATENT DOCUMENTS

| | | | |
|---|---|---|---|
| 5,730,969 A | | 3/1998 | Hora et al. .................... 424/85 |
| 5,747,445 A | * | 5/1998 | Backstrom et al. ............. 514/4 |
| 5,814,607 A | | 9/1998 | Pattson ........................ 514/12 |
| 5,830,853 A | * | 11/1998 | Backstrom et al. ............. 514/4 |
| 5,858,968 A | | 1/1999 | Weiner et al. ................. 514/4 |
| 5,952,008 A | | 9/1999 | Backström et al. ............. 514/3 |
| 5,997,848 A | | 12/1999 | Patton et al. ................. 424/46 |
| 6,004,574 A | | 12/1999 | Backström et al. ........... 424/46 |
| 6,051,256 A | | 4/2000 | Platz et al. ................. 424/489 |
| 6,165,976 A | | 12/2000 | Backström et al. ......... 424/489 |
| 6,306,440 B1 | | 10/2001 | Backström et al. |

FOREIGN PATENT DOCUMENTS

| | | |
|---|---|---|
| EP | 0 128 831 | 12/1984 |
| EP | 0 133 252 A2 | 2/1985 |
| EP | 0 200 383 | 7/1986 |
| EP | 200383 * | 12/1986 |
| EP | 0 225 189 | 10/1987 |
| EP | 0 312 052 A1 | 10/1987 |
| EP | 0 364 235 A1 | 4/1988 |
| EP | 0 272 097 | 6/1988 |
| EP | 0 360 340 | 3/1990 |
| EP | 0 455 463 | 11/1991 |
| EP | 0 383 751 | 9/1994 |
| GB | 837465 | 6/1960 |
| GB | 1 242 211 | 8/1971 |
| GB | 1 527 605 | 4/1978 |
| GB | 1 520 247 | 8/1978 |
| GB | 1 569 611 | 6/1980 |
| JP | 1117825 | 2/1987 |
| JP | 632932 | 7/1988 |
| JP | 4041421 | 6/1990 |
| JP | 4-41421 | 2/1992 |
| JP | 4149126 | 5/1992 |
| JP | 4-149126 | 5/1992 |
| SE | 8007820 | 11/1986 |
| SE | 9 302 198-8 | 6/1993 |
| SE | 9 400 371-2 | 2/1994 |
| WO | WO 87/05213 | 9/1978 |
| WO | WO 88/09163 | 12/1988 |
| WO | 90/04962 | 5/1990 |
| WO | WO90/07333 | 7/1990 |
| WO | WO 91/16038 | 10/1991 |
| WO | 91/16882 | 11/1991 |
| WO | 91/16929 | 11/1991 |
| WO | WO 91/18091 A1 | 11/1991 |
| WO | WO 92/04069 | 3/1992 |
| WO | WO 92/06704 | 4/1992 |
| WO | WO92/08446 | 5/1992 |
| WO | 93/25198 | 12/1993 |
| WO | 94/07514 | 4/1994 |
| WO | WO 94/07514 | 4/1994 |
| WO | 94/22461 | 10/1994 |
| WO | WO 95/00128 | 1/1995 |
| WO | 95/00151 | 1/1995 |
| WO | WO 96/19206 | 6/1996 |
| WO | WO 96/19207 | 6/1996 |
| WO | WO 97/10850 | 3/1997 |

OTHER PUBLICATIONS

Byron et al., "Drug Delivery via the Respiratory . . . ," Journal of Aerosol Medicine, 7:49–75, 1994.

Nagano et al., "New Method of Insulin . . . ," Jikeikai Med. J., 32:503–506, 1985.

Elliott et al., "Parenteral absorption of insulin . . . ," Aust. Paediatr. J., 23:293–297, 1987.

Sakr., "A new approach for insulin . . . ," International Journal of Pharmaceutics, 86:1–7, 1992.

Liu et al., "Pulmonary Delivery of Free . . . ," Pharmaceutical Research , 10:228–232, 1993.

Dieter Köhler, "Aerosols for Systemic Treatment," Lung Suppl:677–684, 1990.

Jacobs et al, "The Pharmacodynamics and . . . ," Diabetes, 42:1649–1655, 1993.

Aungst et al, "Comparison of Nasal . . . ," The Journal of Pharmacology and Experimental Therapeutics, 244:23–27, 1987.

Köhler et al., "Pulmonary Administration . . . ," Abstract 298, Diabetes 33 (Suppl.):75A, 1984.

Hoover et al, "Peptides are Better . . . ," Pharmaceutical Research, 9(8):1103–1106, 1992.

Colthorpe et al, "The Pharmacokinetics . . . ," Pharmaceutical Research, 9(6):pp. 764–768, 1992.

Köhler et al, "Nicht radioaktives . . . ," Atemw–Lungenkrkh., Jahrgang 13, Nr. 6/1987, S. 230–232.

Chien et al, "Potential Developments in . . . ," Drug Development and Industrial Pharmacy, 15(10):1601–1634, 1989.

Patton et al, "(D) Routes of Delivery: Case Studies," Advanced Drug Delivery Reviews, 8:179–196, 1992.

Li et al., "Effect of a . . . ," Eur. J. Pharm. Biopharm., 39:216–221, 1993.

Chien et al., "Intranasal Drug Delivery for Systemic Medications", CRC Critical Reviews in Therapeutic Drug Carrier Systems 4:67–194, 1987.

Eppstein et al., "Alternative Delivery Systems for Peptides and Proteins As Drugs", CRC Critical Reviews in Therapeutic Drug Carrier Systems 5:99–139, 1988.

O'Hagan et al., "Absorption of Peptides and Proteins from the Respiratory Tract and the Potential for Development of Locally Administered Vaccine", Critical Reviews in Therapeutic Drug Carrier Sys 7:35–97, 1990.

Allenby et al., The Absorption of Insulin Across the Respiratory Tract of the Guinea–Pig (U), The Aerosol Society, Fourth Annual Conference 1990, pp. 129–134.

Aungst and Rogers, Comparison of the Effects of Various Transmucosal Absorption Promoters on Buccal Insulin Delivery, Int. J. Pharm. (Netherlands), 1989, 53/3, 227–235.

Björk, Starch Microspheres as a Nasal Delivery System for Drugs, Comprehensive Summaries of Uppsala Dissertations from the Faculty of Pharmacy 103, 1993.

Björk and Edman, Degradable Starch Microspheres as a Nasal Delivery System for Insulin, Int. J. Pharm. 47:233–238, 1988.

Brange et al., Monomeric Insulins and Their Experimental and Clinical Implications, Diabetes Care 13:923–954, 1990.

Edman and Björk, Routes of Delivery: Case Studies, Advanced Drug Delivery Reviews 8:165–177, 1992.

Igawa et al., Effect of Absorption Promoters in Intranasal Administration of Human Fibroblast Interferon as a Powder Dosage Form in Rabbits, Chem. Pharm. Bull. 37:418–421, 1989.

Komada et al., Intratracheal Delivery of Peptide and Protein Agents: Absorption from Solution and Dry Powder by Rat Lung, J. Pharm. Sci. 83:863–867, 1994.

Lasker, The Diabetes Control and Complications Trial, N. Engl. J. Med. 329:1035–1036, 1993.

Laube et al., Preliminary Study of the Efficacy of Insulin Aerosol Delivered by Oral Inhalation in Diabetic Patients, JAMA 269:2106–2109, 1993.

Lee et al., Intranasal Bioavailability of Insulin Powder Formulations: Effect of Permeation Enhancer–to–Protein Ratio, J. Pharm. Sci. 80:725–729, 1991.

Misima et al., Studies on the Promoting Effects of Medium Chain Fatty Acid Salts on the Nasal Absorption of Insulin in Rats, J. Pharma –Dyn. 10:624–631, 1987.

Morita et al., Effects of Various Absorption Promoters on Pulmonary Absorption of Drugs with Different Molecular Weights, Biol. Pharm. Bull. 16:269:262, 1993.

Nagai et al., Powder Dosage Form of Insulin for Nasal Administration, J. Controlled Release 1:15–22, 1984.

"Diabetes Mellitus", Ch. VI in Scientific American Medicine, Scientific American, Inc., Apr. 1993.

The Diabetes Control and Complications Trial Research Group, The Effect of Intensive Treatment of Diabetes on the Development . . . Complications in Insulin–Dependent Diabetes Mellitus, N. Eng. J. Med. 329:977–86, 1993.

Pontiroli et al., Nasal Administration of Glucagon and Human Calcitonin to Healthy Subjects: a Comparison of Powders and Spray Solutions and of Different Enhancing Agents, Eur. J. Clin. Pharmacol. 37:427–430, 1989.

Schipper et al., Nasal Insulin Delivery with Dimethyl–β–Cyclodextrin as an Absorption Enhancer in Rabbits: Powder More Effective than Liquid Formulations, Pharmaceutical Research 10:682–686, 1993.

Selam and Charles, Devices for Insulin Administration, Diabetes Care 13:955–979, 1990.

Touitou and Rubenstein, Targeted Enteral Delivery of Insulin to Rats, Int. J. Pharm. (Amst.), 30(2–3), 1986, 95–100.

Wigley et al., Insulin Across Respiratory Mucosae by Aerosol Delivery, Diabetes 20:552–556, 1971.

Zinman, Medical Intelligence—The Physiologic Replacement of Insulin, N. Engl. J. Med. 321:363–370, 1989.

Olanoff et al., "Method to Enhance Intranasal Peptide Delivery," in "Controlled–Release Technology Pharmaceutical Applications," Lee et al., American Chemical Societ, 301–309, 1987.

Timsina et al., Drug Delivery to the Respiratory Tract Using Dry Powder Inhalers, Int. J. Pharmaceutics 101:1–13 (1994).

Wearley, Recent Progress in Protein and Peptide Delivery by Noninvasive Routes, Critical Rev. Therapeut. Drug Carrier Systems 8:331–394 (1991).

Dahlbäck et al., Regional Administration of Drugs to the Rabbit Respiratory Tract, Effects on Absorption, J. Aerosol Medicine 1:222–223 (1988).

Damasy et al., Diabetes Res. and Clin. Pract. 5:S163 (1988).

Hirai et al., Effect of Surfactants on the Nasal Absorption of Insulin in Rats, Int. J. Pharmaceutics 9:165–172 (1981).

Moses et al., Insulin Administered Intranasally as an Insulin–Bile Salt Aerosol, Diabetes 32:1040–47 (1983).

Almer et al., Insulin Inhalation—At Last A Break–Through, Diabetes Res. Clin. Pract. 5:S163–POS–001–169, 1988.

Chandler et al., Nasal Absorption in Rats. II. Effect of Enhancers on Insulin Absorption and Nasal Histology, Int'l J. Pharmaceutics, 76:61–70, 1991.

Cutie et al., The Role of Dispersing Agents in Inhalation and Intranasal Aerosol Suspensions, Aerosol Age, pp. 52–54, 1985.

Dahlback et al., Deposition of Tracer Aerosols in the Rabbit Respiratory Tract, J. Aerosol Sci., vol. 18, No. 6, pp. 733–736, 1987.

Gordon et al., Nasal Absorption of Insulin: Enhancement by Hydrophobic Bile Salts, Proc. Nat'l. Acad. Sci. USA, 82:7419–23, 1985.

Lee et al., Mucosal Penetration Enhancers For Facilitation of Peptide and Protein Drug Absorption, Critical Reviews in Therapeutic Drug Carrier Systems, 8(2):91–192, 1991.

Ruin, Diabetes May Not Need Their Insulin Shots, article in Sydsvenska [Dagbladet], Monday, Jun. 12, 1989. (English translation attached).

Schanker et al., Species Comparison of Drug Absorption from the Lung After Aerosol Inhalation or Intratracheal Injection, Drug Metabolism & Disposition, vol. 14, pp. 79–88, 1986.

Yoshida et al., Absorption of Insulin Delivered to Rabbit Trachea Using Aerosol Dosage Form, J. Pharm. Sci. 68:670, 1979.

Remington's Pharmaceutical Science, 18th edn., p. 1079 (1990).

Longenecker et al., Effects of Sodium Taurodihydrofusidate on Nasal Absorption of Insulin in Sheep, J. Pharm. Sci., 76(5):351–355 (1987).

Mizgala et al., Renal Handling of Phosphate, Physiological Reviews, 65(2):431–466 (1985).

Salzman et al., Intranasal Aerosolized Insulin Mixed–Meal Studies and Long–term Use in Type I Diabetes, The New England Journal of Medicine, 312:1078–1084, 1985.

Zingg et al., Transhepatic Absorption and Biliary Excretion of Insulin, Can. J. Physiol. Pharmacol., 65:1982–1987 (1987).

Bjork et al., "Characterization of degradable starch........", Int. J. Pharmaceutics, 62 (1990) 187–192.

Jones, "Pulmonary Absorption of Insulin", (1998) Ph. D. Thesis, Welsh School of Pharmacy, University of Wales, United Kingdom.

Lee et al., "Development of an Aerosol Dosage Form Containing Insulin", J. Pharmaceutical Sciences, vol. 65, No. 4, (1976) 567–574.

Newman, "Chapter 9: Therapeutic aerosols", In: Aerosols and the Lung: Clinical and Experimental Aspects, (1984) Butterworth & Co., United Kingdom.

Dempster et al., Anabolic Actions of Parathyroid Hormone on Bone, *Endocrine Reviews* 14: 690–709, (1993).

Goni et al., "Palmitoylcarnitine, a surface–active metabolite," *FEBS Lett.*, vol. 390, pp. 1–5 (1996).

Jaegfeldt, H. et al., "Particle size distribution from different modifications of Turbuhaler®," Proceedings of an international workshop on a new inhaler, May 21–22, 1987 (London) pp. 90–99.

Lecluyse et al., "In Vitro Effects of Long–Chain Acylcarnitines on the Permeability, Transepithelial Electrical Resistance and Morphology of Rat Colonic Mucosa," *J. Pharmacol. Exp. Ther.*, vol. 265(2), pp. 955–962 (1993).

Okumura et al., "Intratracheal delivery of insulin absorption from solution and aerosol by rat lung," *International Journal of Pharmaceutics*, vol. 88, pp. 63–73 (1992).

Patton et al., "(D) Routes of Delivery: Case Studies," *Advanced Drug Delivery Reviews*, vol. 8, pp. 179–196 (1992).

Reeve et al., Anabolic Effect on Human Parathyroid Hormone Fragment on Trabecular Bone in Involutional Osteoporosis: A Multicentre Trail, British Medical Journal, pp. 1340–1344, (1980).

Schluter et al., "Pulmonary Administration... Type 1 Diabetics" Abstract #298, *Diabetes*, 33 (Supplement): 75A (1984).

Wang et al., *Parenteral Science and Technology*, 42 (2S), S4–S26, 1988.

Wetterlin, Kiell, "Turbuhaler: A New Powder Inhaler for Administration of Drugs to the Airways," *Pharmaceutical Research*, vol. 5, pp. 506–508, (1988).

Yamamoto et al., "Absorption Enhancement of Intrapulmonary Administered Insulin by Various Absorption...," *J. Pharm. Pharmacol.*, vol. 46, pp. 14–18 (1994).

* cited by examiner

Transport of mannitol across Caco-2 cell monolayer in presence of Na-caprate (10-16mM)

A. Na-caprate
B. Na-caprate/insulin (1:3 w/w)

SYSTEMIC ADMINISTRATION OF A THERAPEUTIC PREPARATION

This is a continuation of U.S. application Ser. No. 08/582,702, filed Jan. 4, 1996, now U.S. Pat. No. 5,830,853, which is a continuation-in-part of U.S. application Ser. No. 08/265,371, filed Jun. 23, 1994, now U.S. Pat. No. 5,506,203.

BACKGROUND OF THE INVENTION

Diabetes mellitus (commonly referred to simply as diabetes) is a disease characterized by disregulation of metabolism, particularly glucose metabolism. In normal individuals, a rise in blood glucose levels (such as that which occurs immediately following eating) triggers the islet beta cells of the pancreas to secrete insulin, a peptide hormone, into the bloodstream. The insulin binds to insulin receptors located on a number of cell types, notably muscle cells, and thereby signals the cells to increase the rate of glucose uptake into the cells. As the blood glucose returns to normal pre-prandial levels, the amount of insulin in the blood also drops. In the absence of insulin, blood glucose levels would rise to dangerously high levels (a condition termed hyperglycemia), possibly resulting in death. Too much insulin causes abnormally low blood glucose levels (hypoglycemia), which is also dangerous and possibly fatal. In a normal individual, built-in feedback loops regulating the secretion of insulin and its clearance from the systemic circulation prevent both hyperglycemic and hypoglycemic conditions from occurring.

Type I diabetes, or insulin-dependent diabetes mellitus (IDDM), usually begins in childhood. It is a disease affecting approximately one in 250 individuals in the United States. Type I diabetes is characterized by atrophy of the pancreatic beta cells, resulting in a decrease or cessation of insulin production, and leaving the patient dependent on exogenous insulin for survival.

Far more common is Type II diabetes, or non-insulin-dependent diabetes mellitus (NIDDM), which generally occurs in patients older than 40 years. These patients may, at least initially, have normal or even high levels of insulin in their blood, but exhibit an abnormally low rate of cellular uptake of glucose in response to insulin. Although Type II diabetes often can be treated by controlling the patient's diet, administration of exogenous insulin to supplement that secreted by the patient's beta cells may also prove necessary.

Ideally, exogenous insulin would be administered at times and in doses that would yield a plasma profile which mimics the natural plasma profile of endogenously secreted insulin in a normal individual, thereby avoiding both hyperglycemic and hypoglycemic states. Insulin is typically administered at set times (e.g., before meals and/or bedtime), or, if blood glucose is monitored, whenever the patient's blood glucose level appears high. The standard method of administration is by subcutaneous injection of a saline solution of insulin, usually by the patient him/herself. This method deposits a reservoir of the insulin-containing solution under the patient's skin, and permits gradual absorption of the solution into the bloodstream via the dermal capillaries. According to the Merck Index, 11th Edition, Budavari et al., Ed., Merck & Co., Inc., N.J. (1989), insulin formulated for s.c. injection reaches its maximum activity at 2 to 3 hours following injection; duration of effect is said to be 6 to 8 hours. Certain slow-acting formulations of insulin (e.g., Lente insulin) show an even more prolonged effect.

Figure 1:
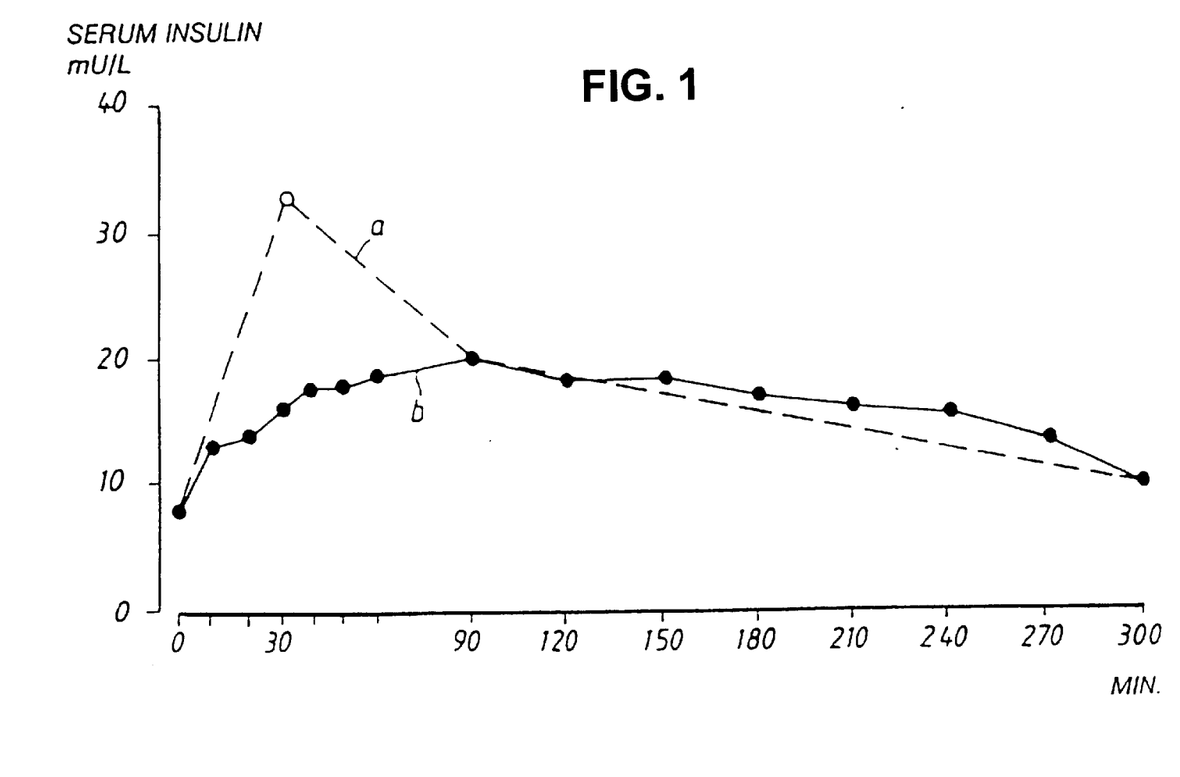
FIG. 1 is a graph showing changes in plasma insulin levels in (a) a non-diabetic individual following ingestion of a meal at time zero (data adapted from Arnqvist et al., Acta. Med. Scand., 1986, 220, 133–141), and (b) an individual with Type I diabetes, following injection of 10 units of insulin at time zero (data adapted from FIG. 1 of Diabetes Care, vol. 5, No. 2, 1982, Berger). The two sets of data from different sources are shown together to facilitate comparison.
Figure 2:
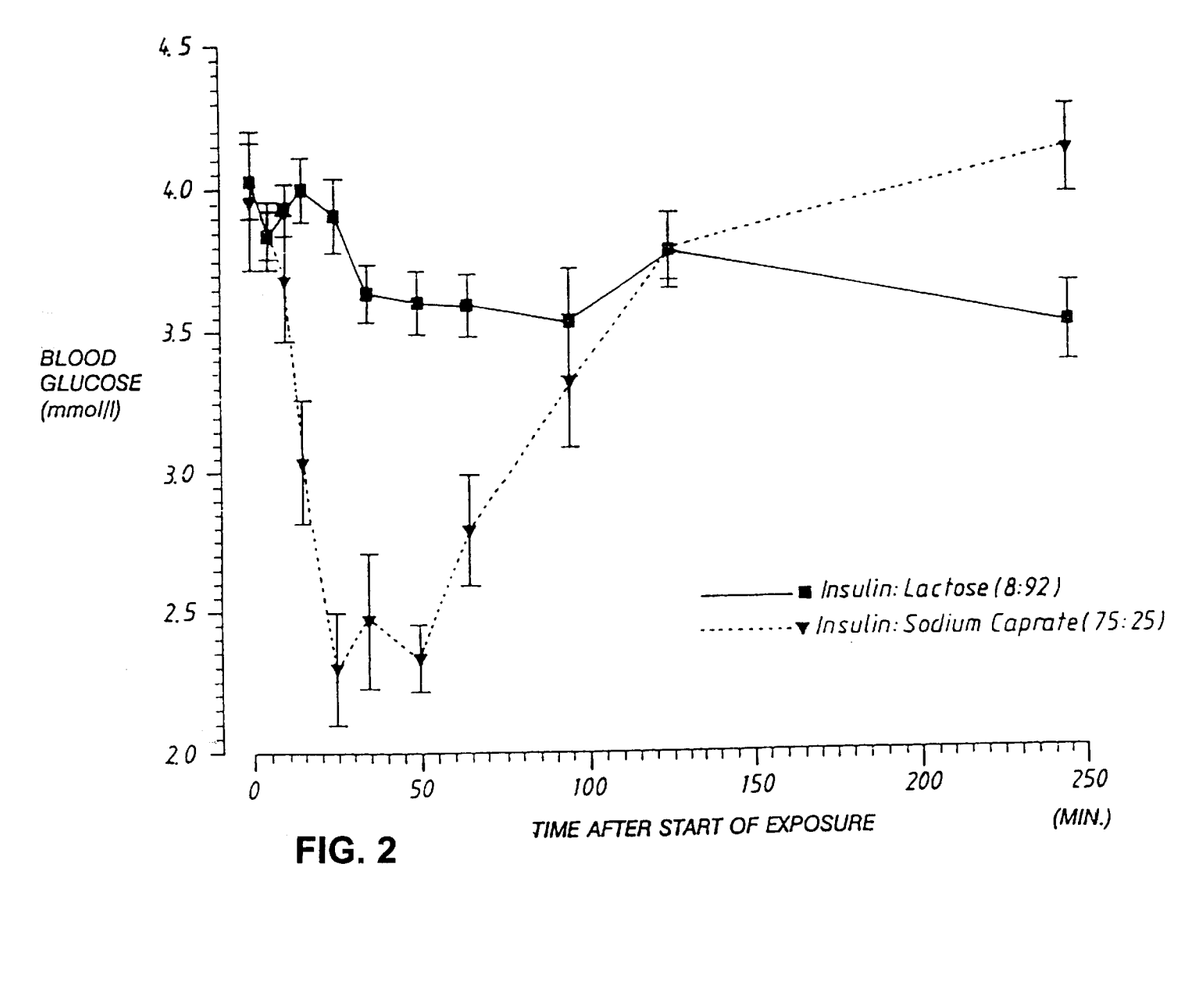
FIG. 2 is a graph showing the effects of inhaling insulin-containing preparations on plasma insulin levels in dogs. Shown are data for inhalation of insulin:lactose (8:92) (with no enhancer) and insulin:sodium caprate (75:25). Each dog received five minutes of exposure to a preparation containing 1 U. insulin/kg body weight. (1U.=1 unit of human insulin=35 µg human insulin, 100%)
Figure 3:
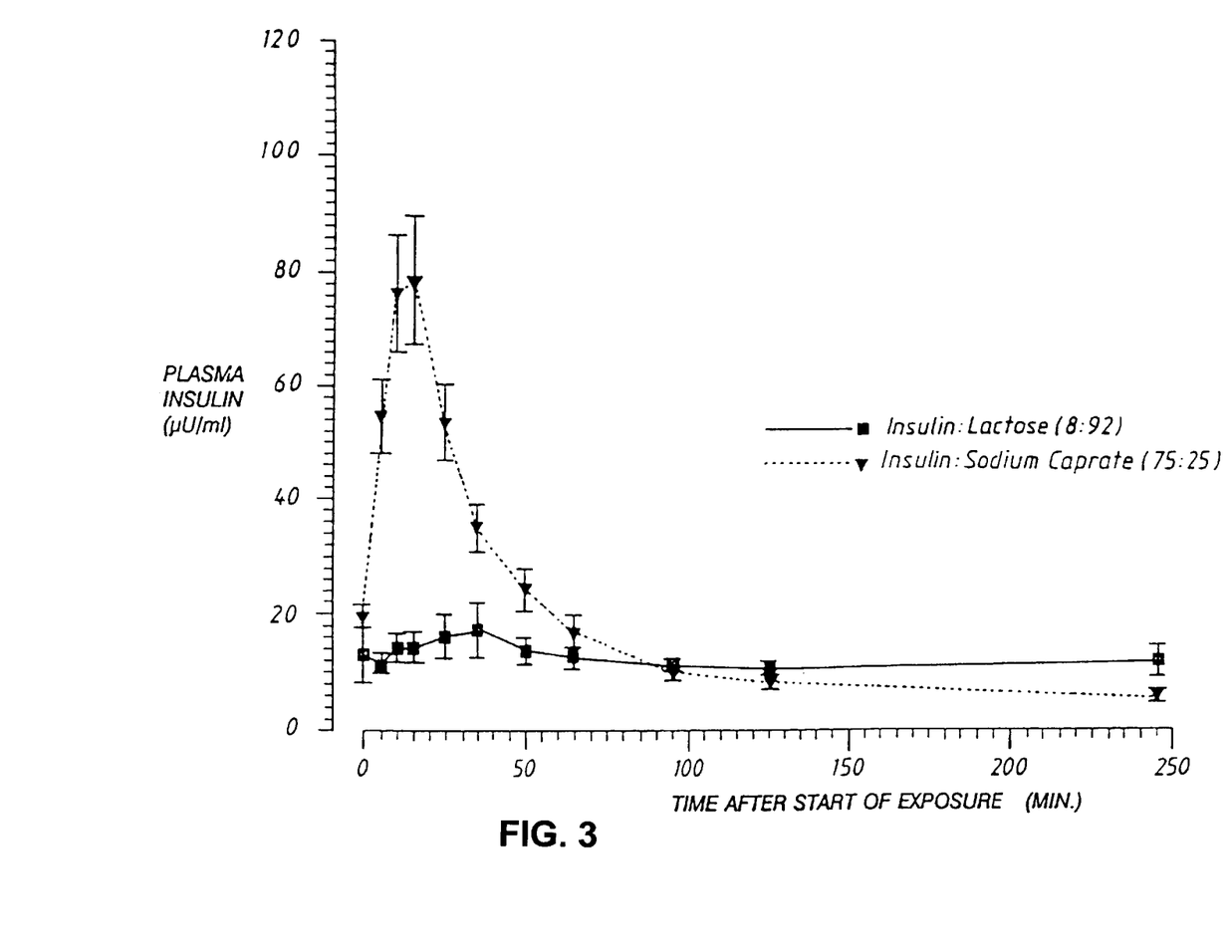
FIG. 3 is a graph showing the effect of inhalation of insulin-containing preparations on blood glucose levels in the experiments shown in FIG. 2.
Figure 4:
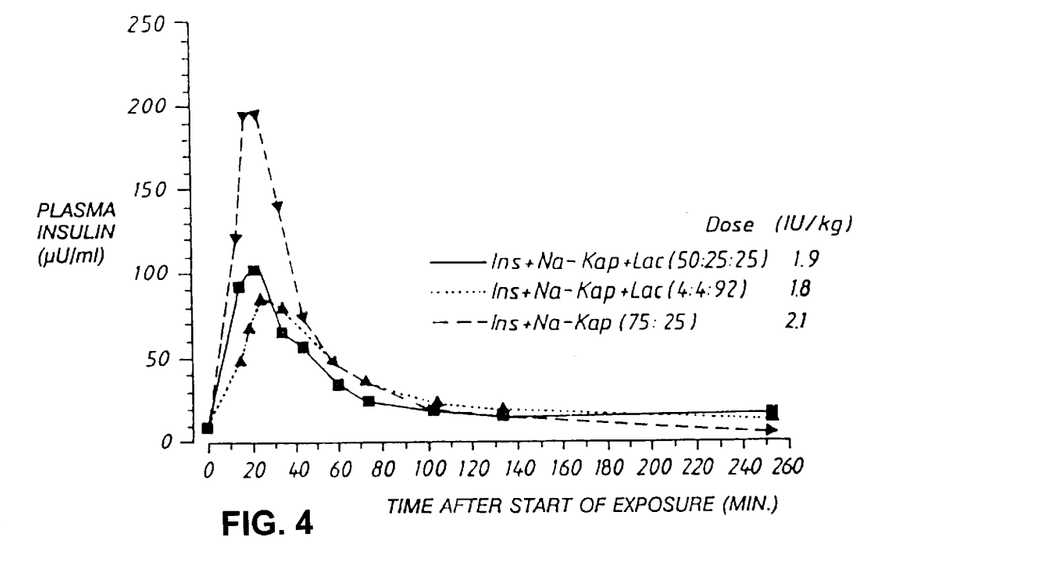
FIG. 4 is a graph showing the effects of inhaling each of three different insulin/sodium caprate formulations on plasma insulin levels in a single experimental animal.
Figure 5:
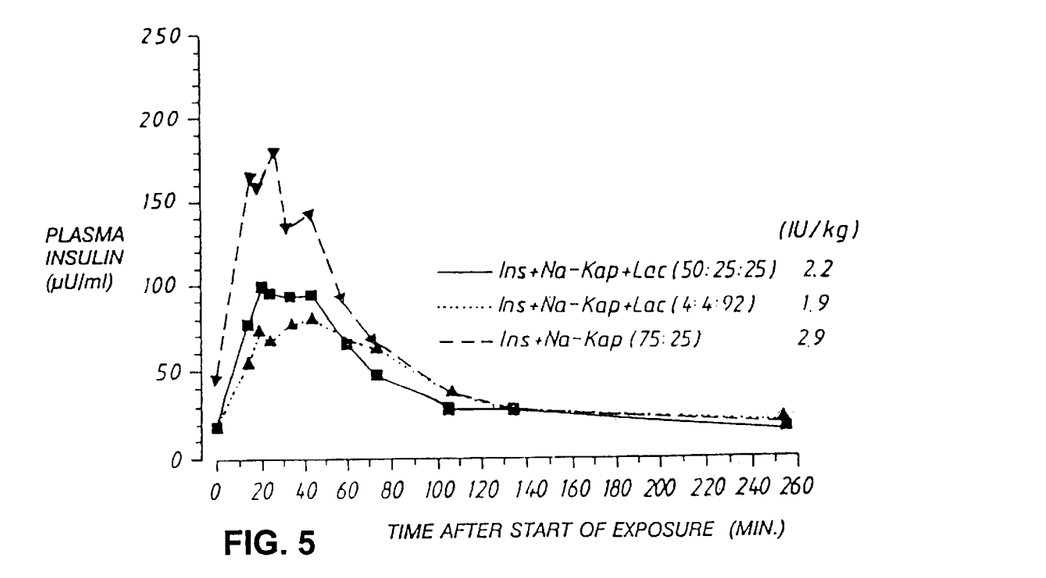
FIG. 5 is a graph showing the effects of inhaling each of three different insulin/sodium caprate formulations on plasma insulin levels in a second experimental animal.

Shown in FIG. 1 is a graph illustrating (a) the postprandial pharmacokinetic profile of plasma insulin for a normal individual (data adapted from Arnqvist et al., Acta. Med. Scand., 1986, 220, 133–141), and (b) the pharmacokinetic profile of plasma insulin for a Type I diabetic given a subcutaneous injection of insulin (data adapted from FIG. 1 of Diabetes Care, Vol. 5, No. 2, 1982, Berger).

SUMMARY OF THE INVENTION

It has been found that when insulin is combined with an appropriate absorption enhancer and is introduced into the lower respiratory tract in the form of a powder of appropriate particle size, it readily enters the systemic circulation by absorption through the layer of epithelial cells in the lower respiratory tract. This is conveniently accomplished by inhalation of the powder containing insulin and the absorption enhancer (hereinafter collectively referred to as the active compounds) from an inhaler device. which dispenses the correct dose of powdered active compounds in a particle size which maximizes deposition in the lower respiratory tract, as opposed to the mouth and throat. To accomplish this preferential delivery into the lower respiratory tract, as much as possible of the inhaled active compounds should consist of particles with a diameter less than approximately 10 $\mu$m (e.g., between 0.01–10 $\mu$m, and ideally between 1–6 $\mu$m). In preferred embodiments, at least 50% (preferably at least 60%, more preferably at least 70%, still more preferably at least 80%, and most preferably at least 90%) of the total mass of the active compounds which exits the inhaler device consists of particles within the desired diameter range. The plasma pharmacokinetics (i.e., the rate of appearance and disappearance in the plasma) of insulin delivered by the method of the invention has been found to resemble more closely the plasma pharmacokinetics of endogenous insulin secreted by a healthy individual in response to glucose challenge or a meal, than does the plasma pharmacokinetics of human insulin delivered by subcutaneous injection, the standard route of insulin delivery. This is believed to occur because a dose of insulin delivered in accordance with the invention is absorbed much more rapidly into the systemic circulation than is a dose of subcutaneously injected insulin. The method of the invention therefore offers the ability rapidly to produce a transient rise in blood insulin in accordance with the needs of the patient, without a concominant persistance of artificially high blood insulin concentrations long after the transient reqirement for insulin is satisfied. In addition, the method of the invention also has the advantage of simple and painless delivery of the insulin dosage.

The invention thus features a method of treating a patient in need of insulin treatment, which method includes the step of introducing into the lower respiratory tract of the patient an effective amount of active compounds (a) insulin (e.g., human insulin) and (b) an enhancer which enhances the absorption of insulin in the lower respiratory tract of the patient, which active compounds may be comprised in a dry powder suitable for inhalation. By "enhances absorption" is meant that the amount of insulin absorbed into the systemic circulation in the presence of the enhancer is higher than the amount absorbed in the absence of enhancer.

At the point the powder enters the respiratory system of the patient, at least 50% of the total mass of the active compounds therein preferably consists of particles having a diameter of about 10 microns or less. Where the powder is supplied as agglomerates of such particles, contained in an inhaler device, the agglomerates should be substantially deagglomerated prior to entry into the respiratory system of the patient. This may be accomplished, for example, by use of an inhaler device in which the agglomerates are substantially deagglomerated by air turbulence created within the device upon inhalation from the device by the patient. Where the powder is supplied as an ordered mixture of active compounds and pharmaceutically acceptable carrier, the active compounds should be released from the large particles preferably upon inhalation, either by mechanical means in the inhaler device or simply by the action of inhalation, or by other means, the active compounds then being deposited in the lower respiratory tract and the carrier particles in the mouth.

The inhaler device is suitably a dry powder inhaler device and is preferably a single-dose, dry powder inhaler device.

The enhancer of the invention is preferably a surfactant, such as a salt of a fatty acid, a bile salt, or a phospholipid. The enhancer may be, for example, a sodium, potassium, or organic amine (e.g., lysine) salt of the fatty acid, and the fatty acid is preferably capric acid or another fatty acid of 8–16 carbon atoms. The preferred fatty acid salt is sodium caprate. The ratio of insulin to enhancer will preferably vary from about 9:1 to about 1:1.

DETAILED DESCRIPTION

A number of preferred embodiments of the invention are described below.

Insulin

The insulin may be any form or derivative of insulin that is biologically active in the animal being treated. For a human patient, the insulin is preferably human [e.g., recombinant, naturally occurring, or semisynthetic (in which the terminal alanine of the B chain of porcine insulin is chemically replaced with threonine, to yield a molecule identical to human insulin)], porcine, bovine, or a biologically active derivative of human insulin having certain amino acid substitutions as taught by Brange et al., Diabetes Care 13:923, 1990 (herein incorporated by reference). The insulin should have a low zinc content, since zinc decreases the solubility (and thus the dissolution rate) of insulin, and may form insoluble precipitates with certain enhancers.

Enhancer

The enhancer used can be any of a number of compounds which act to enhance absorption through the layer of epithelial cells lining the alveoli of the lung, and into the adjacent pulmonary vasculature. The enhancer can accomplish this by any of several possible mechanisms, including the following:

(1) Enhancement of the paracellular permeability of insulin by inducing structural changes in the tight junctions between the epithelial cells.

(2) Enhancement of the transcellular permeability of insulin by interacting with or extracting protein or lipid constituents of the membrane, and thereby perturbing the membrane's integrity.

(3) Interaction between enhancer and insulin which increases the solubility of insulin in aqueous solution. This may occur by preventing formation of insulin aggregates (dimers, trimers, hexamers), or by solubilizing insulin molecules in enhancer micelles.

(4) Decreasing the viscosity of, or dissolving, the mucus barrier lining the alveoli and passages of the lung, thereby exposing the epithelial surface for direct absorption of the insulin.

Enhancers may function by only a single mechanism set forth above, or by two or more. An enhancer which acts by several mechanisms is more likely to promote efficient absorption of insulin than one which employs only one or two. For example, surfactants are a class of enhancers which are believed to act by all four mechanisms listed above. Surfactants are amphiphilic molecules having both a lipophilic and a hydrophilic moiety, with varying balance between these two characteristics. If the molecule is very lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity.

Another surfactant property that may be of importance is the net charge of the surfactant at the pH value in the lung (approximately 7.4). The isoelectric pH of insulin is 5.5. At pH 7.4, insulin has a negative net charge. This results in an electrostatic repulsion between insulin molecules, which in turn prevents aggregation and thereby increases the solubility. If the surfactant also is negatively charged, yet can interact with insulin by, for example, hydrophobic interactions, additional repulsion among the insulin molecules will occur. Therefore, an anionic surfactant will possess the additional advantage (compared to those having neutral or net positive charge at physiological pH) of enhancing absorption by helping stabilize insulin in the monomeric state.

One very promising type of enhancer is the salt of a fatty acid. It has been found that the sodium salts of saturated fatty acids of carbon chain length 10 (i.e., sodium caprate), 12 (sodium laurate) and 14 (sodium myristate) perform well in the method of the invention. The potassium and lysine salts of capric acid have also been found to be effective in the method of the invention. If the carbon chain length is shorter then about 8, the surface activity of the surfactant may be too low, and if the chain length is longer than about 16, decreased solubility of the fatty acid salt in water limits its usefulness.

Different counterions may change the solubility of the saturated fatty acid salt in water, such that an enhancer having a carbon length other than 8–16 would prove even more advantageous than the enhancers specifically mentioned hereinabove. Salts of unsaturated fatty acids may also be useful in the present invention since they are more water soluble than salts of saturated fatty acids, and can therefore have a longer chain length than the latter and still maintain the solubility necessary for a successful enhancer of insulin absorption.

All of the bile salts and bile salt derivatives tested (sodium salts of ursodeoxycholic acid, taurocholic acid, glycocholic acid, and taurodihydrofusidic acid) effectively enhance insulin absorption in the lung. Examples of suitable bile salts include salts (e.g., sodium or potassium salts) of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid. Preferred are the trihydroxy bile salts, such as the salts (e.g., potassium and sodium salts) of cholic, glycocholic and taurocholic acids. Particularly preferred are sodium taurocholate and potassium taurocholate.

Phospholipids were also tested as enhancers. It was found that a single-chain phospholipid (lysophosphatidylcholine) was an effective enhancer, while one double-chain phospholipid (didecanoylphosphatidylcholine) was not. This may be explained by the fact that the double-chain phospholipid is much less soluble in water than their single-chain counterpart; however, it is reasonable to expect that double-chain phospholipids of shorter chain length, having greater water-solublility than their longer chain counterparts, will be of use as enhancers in the present invention so that both single- and double-chain phospholipids may be used. Examples of single-chain phospholipids include lysophosphatidylcholine, lysophosphatidylglycerol, palmitoylphosphatidylglycerol, palmitoylphosphatidylcholine, lysophosphatidylethanolamine, lysophosphatidylinositol, and lysophosphatidylserine. Examples of double-chain phospholipids include diacylphosphatidylcholine, diacylphosphatidylglycerol, diacylphosphatidylethanolamine, diacylphosphatidylinositol, and diacylphosphatidylserine.

One glycoside, octylglucopyranoside, was tested as an enhancer in the present invention and was found to have some absorption enhancing properties. Other alkyl glycosides such as the alkyl glucosides (e.g., decyl glucoside, dodecyl glucoside, and alkyl thioglucopyranoside) and alkyl maltosides (e.g., decyl maltoside and dodecyl maltoside) would also be expected to exhibit absorption enhancing properties in the methods of the present invention.

The cyclodextrins and derivatives thereof effectively enhance the nasal absorption of insulin, and may function similarly in the lung. Dimethyl-β-cyclodextrin has been tested in the method of the present invention and has been found to have an absorption enhancing effect.

Other potentially useful surfactants are sodium salicylate, sodium 5-methoxysalicylate, and the naturally occurring surfactants such as salts (e.g., sodium and potassium salts) of glycyrrhizine acid, saponin glycosides, and acyl carnitines such as decanoyl carnitine, lauryl carnitine, myristoyl carnitine, and palmitoyl carnitine.

For ionic enhancers (e.g., the anionic surfactants described above), the nature of the counterion may be important. The particular counterion selected may influence the powder properties, solubility, stability, hygroscopicity, and local/systemic toxicity of the enhancer or of any formulation containing the enhancer. It may also affect the stability and/or solubility of the insulin with which it is combined. In general, it is expected that monovalent metallic cations such as sodium, potassium, lithium, rubidium, and cesium will be useful as counterions for anionic enhancers. Ammonia and organic amines form another class of cations that is expected to be appropriate for use with anionic enhancers having a carboxylic acid moiety. Examples of such organic amines include ethanolamine, diethanolamine, triethanolamine, 2-amino-2-methylethylamine, betaines, ethylenediamine, N,N-dibensylethylenetetraamine, arginine, hexamethylenetetraamine, histidine, N-methylpiperidine, lysine, piperazine, spermidine, spermine, and tris (hydroxymethyl)aminomethane.

Since effective enhancement of insulin absorption in the lower respiratory tract was observed for a number of the enhancers tested, it is expected that many more will be found which also function in this manner. Starch microspheres effectively enhance the bioavailability of insulin delivered via the nasal membranes and were tested as an enhancer in the methods of the invention. Although they proved to be of little use for delivery via the pulmonary route in the animal model utilized herein, it is thought that this was mainly due to technical difficulties which, if overcome, may lead to successful delivery via the pulmonary route. Chelators are a class of enhancers that are believed to act by binding calcium ions. Since calcium ions help maintain the dimensions of the space between cells and additionally reduce the solubility of insulin, binding of these ions would in theory both increase the solubility of insulin, and increase the paracellular permeability of insulin. Although one chelator tested, the sodium salt of ethylenediaminetetraacetic acid (EDTA), was found to be ineffective in enhancing absorption of insulin in the rat model tested, other calcium ion-binding chelating agents may prove to be more useful.

A number of different compounds potentially useful as enhancers in the methods of the invention were tested in rats, as described in Example 5 below. Other substances with known absorption-enhancing properties, or with physical characteristics which make them likely candidates for use in the method of the invention, can be readily tested by one of ordinary skill in that in vivo assay, or alternatively in the in vitro assay described in Example 6.

It is possible that a combination of two or more enhancer substances also gives satisfactory results. The use of such a combination in the method of the invention is considered to be within the invention.

An enhancer useful in the methods of the invention will combine (1) effective enhancement of insulin absorption with (2) lack of toxicity in the concentrations used and (3) good powder properties, i.e., lack of a sticky or waxy consistency in the solid state. Toxicity of a given substance can be tested by standard means, such as an MTT assay, as for example described in Int.J.Pharm. 65 (1990) 249–259. The powder properties of a given substance may be ascertained from published data on the substance, or empirically.

Proportions of Insulin and Enhancer

In general, it is desirable to keep the ratio of insulin to enhancer as high as possible, within the range that permits fast and efficient enhancement of insulin absorption. This is important in order to minimize the risk of adverse effects, both local and systemic, attributable to the enhancer. The optimal ratio of insulin to enhancer can be ascertained for any given enhancer by testing various proportions in an in vivo model such as described herein. For example, insulin was combined with sodium caprate in the following w/w proportions: 50/50, 75/25, 82.5/17.5, and 90/10. Significant improvement in absorption of insulin was obtained with 50% and 25% sodium caprate; 10% gave poor improvement in absorption, and the results with 17.5% were intermediate. This indicates that the lowest effective concentration of sodium caprate for use in the methods of the invention is approximately 15–25%, and probably 20–25%. Other enhancers may have higher or lower optimal concentrations relative to insulin. Each individual enhancer must therefore be separately tested. Based upon the above result, however, it is expected that the optimal proportion of a surfactant type of enhancer will generally be between 10 and 50% of the insulin/enhancer mixture. It should be noted that the above proportions represent the proportion of enhancer relative solely to insulin, and do not take into account any excipients which may be added, for example to improve the powder properties of the formulation.

The amount of insulin absorbed according to the present invention can be significantly higher than the amount absorbed in the absence of enhancer. In Example 4 herein it is shown that a therapeutic preparation according to the present invention, when inhaled, exhibits a bioavailability well over three times greater than that of an inhaled preparation of insulin alone.

Preferably the amount of insulin absorbed according to the present invention is significantly ($p<0.05$) higher than the amount absorbed in the absence of enhancer.

Additive substances commonly included in therapeutic preparations, such as pharmaceutically acceptable carriers, may be included in the theraputic preparation of the present invention. Additive substances may be included for example in order to dilute the powder to an amount which is suitable for delivery from the particular intended powder inhaler; to facilitate the processing of the preparation; to improve the powder properties of the preparation; to improve the stability of the preparation, e.g. by means of antioxidant or pH-adjusting compounds; or to add a taste to the preparation. Any additive should not adversely affect the stability of the insulin or absorption enhancer, or disadvantageously interfere with the insulin absorption. It should also be stable, not hygroscopic, have good powder properties and have no adverse effects in the airways. As examples of potential additives may be mentioned mono-, di-, and polysaccharides, sugar alcohols and other polyols, such as for example lactose, glucose, raffinose, melezitose, lactitol, maltitol, trehalose, sucrose, mannitol and starch. As reducing sugars such as lactose and glucose have a tendency to form complexes with proteins, non-reducing sugars such as raffinose, melezitose, lactitol, maltitol, trehalose, sucrose, mannitol and starch may be preferred additives for use in the present invention. Depending upon the inhaler to be used, the total amount of such additives may vary over a very wide range. In some circumstances little or no additive would be required, whereas for example in the case of an inhaler requiring large powder volumes for operation, a very high percentage of the therapeutic preparation could consist of additive. The amount of additive desirable would be easily determined by a person skilled in the art according to particular circumstances.

A useful mechanism for delivery of the active compounds into the lower respiratory tract of a patient is through a portable inhaler device suitable for dry powder inhalation. Many such devices, typically designed to deliver antiasthmatic or antiinflammatory agents into the respiratory system, are on the market. Preferably the device is a dry powder inhaler of a design which provides protection of the powder from moisture and has no risk of occasional large doses; in addition as many as possible of the following are desired: protection of the powder from light; high respirable fraction and high lung deposition in a broad flow rate interval; low deviation of dose and respirable fraction; low retention of powder in the mouthpiece; low adsorption to the inhaler surfaces; flexibility in dose size; and low inhalation resistance. The inhaler is preferably a single dose inhaler although a multi dose inhaler, preferably such as a multi dose, breath actuated, dry powder inhaler for multiple use, may be employed. Preferably the inhaler used is a unit dose, breath actuated, dry powder inhaler for single use.

The described powder preparation can be manufactured in several ways, using conventional techniques. It may be necessary to micronize the active compounds and, if appropriate (i.e where an ordered mixture is not intended), any carrier, in a suitable mill, for example in a jet mill at some point in the process, in order to produce primary particles in a size range appropriate for maximal deposition in the lower respiratory tract (i.e., under 10 $\mu$m). For example, one can dry mix insulin and enhancer powders, and carrier where appropriate, and then micronize the substances together; alternatively, the substances can be micronized separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible first to dissolve the components in a suitable solvent, e.g. water, to obtain mixing on the molecular level. This procedure also makes it possible to adjust the pH-value to a desired level. It is known that the nasal absorption of insulin is affected by the pH-value of the preparation, with increasing absorption when moving either up or down from the isoelectric point of insulin, which is around 5.5. However, the insulin may be less stable at pH significantly above or below 5.5, and furthermore the pharmaceutically accepted limits of pH 3.0 to 8.5 for inhalation products must be taken into account, since products with a pH outside these limits may induce irritation and constriction of the airways. To obtain a powder, the solvent must be removed by a process which retains the insulin's biological activity. Suitable drying methods include vacuum concentration, open drying, spray drying, and freeze drying. Temperatures over 40° C. for more than a few minutes should generally be avoided, as some degradation of the insulin may occur. Following the drying step, the solid material can, if necessary, be ground to obtain a coarse powder, then, if necessary, micronized.

If desired, the micronized powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range.

Where an ordered mixture is desired, the active compounds may be processed, for example by micronisation, in order to obtain, if desired, particles within a particular size range. The carrier may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfills the said requirements, and may be determined easily by the skilled person according to the particular circumstances.

EXAMPLE 1

9.75 g of semisynthetic human insulin (Diosynth) and 250 ml water is added to a beaker. The pH is lowered to 3.4 with 1 M HCl and then raised to 7.4 with 1 M NaOH in order to dissolve the insulin. 3.25 g sodium caprate (Sigma) is added and the pH is again adjusted to 7.4. The solution is, stirred, and when the solution is clear or weakly opalescent, it is concentrated by evaporation at 37° C. in about 2 days. The obtained solid cake is crushed and then sieved through a 0.5 mm sieve. The powder is micronized in a jet mill to particles with a mass median diameter of about 2 µm. This micronized powder, containing 75% insulin and 25% sodium caprate by weight, is then filled into an inhalation apparatus (Wright Dust Feed Mechanism) and delivered to animals.

The results from an inhalation study in two non-diabetic dogs are summarized in the tables below. Blood glucose and plasma insulin values were measured at the specified time intervals.

TABLE I

| Blood sample time after end of exposure (minutes) | Blood glucose (mmol/L) | Insulin conc. (µU/ml) |
|---|---|---|
| before | 3.9 | 6.70 |
| 0.5 | 3.6 | 120.66 |
| 5 | 2.8 | 194.47 |
| 10 | 2.6 | 195.39 |
| 20 | n.d. | 139.74 |
| 22.5 | 1.6 | n.d. |
| 31 | 2.0 | 73.42 |
| 45 | 1.7 | 47.49 |
| 59.5 | 1.7 | 36.21 |
| 89.5 | 2.3 | 19.28 |
| 120 | 3.0 | 14.58 |
| 240 | 4.5 | 5.28 | n.d. = not determined

TABLE II

| Blood sample time after end of exposure (minutes) | Blood glucose (mmol/L) | Insulin conc. (µU/ml) |
|---|---|---|
| before | 3.9 | 44.84 |
| 3 | 4.2 | 165.10 |

TABLE II-continued

| Blood sample time after end of exposure (minutes) | Blood glucose (mmol/L) | Insulin conc. (µU/ml) |
|---|---|---|
| 6 | 4.3 | 158.28 |
| 12 | 3.9 | n.d. |
| 14 | n.d. | 180.72 |
| 19 | 3.0 | 133.75 |
| 30 | 2.7 | 143.71 |
| 45 | 2.5 | 91.62 |
| 60 | 2.4 | 66.70 |
| 90 | 2.7 | 38.58 |
| 122 | 3.7 | 29.15 |
| 241 | 4.1 | n.d. |
| 242.5 | n.d. | 19.76 | n.d. = not determined

The tables illustrate that the insulin/sodium caprate formulation markedly increases the plasma level of insulin and decreases the blood glucose. The peak value for plasma insulin and the minimal value for blood glucose are reached after approximately 20 and 60 minutes, respectively.

EXAMPLE 2

A preparation containing semisynthetic human insulin and sodium caprate (75:25 by weight) was prepared as described in Example 1, and introduced into the lungs of five dogs. A control preparation containing insulin and lactose (8:92) but no enhancer was also prepared, and introduced into the lungs of four dogs. The total insulin dose for each dog was 1 U/kg. The effect of each formulation on plasma insulin levels and blood glucose levels was determined at various time points and the results are illustrated in FIGS. 2 and 3. It was found that, while the control formulation containing no enhancer produced essentially no change in plasma insulin levels, the formulation containing both insulin and enhancer produced a rise in plasma insulin levels from about 20 $\mu$U/ml at time zero to about 80 $\mu$U/ml 15 min. after inhalation of the powder. Likewise, the control animals registered a maximal drop in blood glucose of about 0.5 mmol/l following inhalation of insulin without enhancer, while the animals which inhaled insulin plus enhancer registered a transient drop of about 1.7 mmol/l, from about 4.0 mmol/l to about 2.3 mmol/l. Thus, insulin combined with the enhancer, sodium caprate, was quickly absorbed. into and cleared from the systemic circulation, with a corresponding transient decrease in blood glucose levels. In contrast, insulin with carrier (lactose) but no enhancer was detectably absorbed only to a very small degree. (p=0.0002 for insulin/caprate vs. insulin/lactose.)

EXAMPLE 3

Two formulations containing semisynthetic human insulin, sodium caprate and lactose combined in the ratios of 50:25:25 and 4:4:92, respectively, and a third formulation containing human insulin and sodium caprate 75:25, were prepared as described in Example 1; in the formulations containing lactose, solid lactose was added to the insulin/sodium caprate solution prior to final pH adjustment and drying. In the experiments shown in FIGS. 4–7, each of the three formulations was tested in two dogs, at the indicated dosage levels. Plasma insulin and blood glucose were measured at the indicated times following inhalation of the insulin formulation.

EXAMPLE 4

Biosynthetic human insulin (53 g) was micronised in an Airfilco Jet Mill (Trade Mark, Airfilco Process Plant Limited), with pressurised nitrogen (feed pressure 7 bar, chamber pressure 5 bar), to a mass median diameter of 2.4 micrometers.

Sodium caprate (170 g) was micronised in an Airfilco Jet Mill (TM), with pressurised nitrogen (feed pressure 5 bar, chamber pressure 3 bar), to a mass median diameter of 1.6 micrometers.

The micronised biosynthetic human insulin (45 g) and sodium caprate (14.26 g) were dry mixed according to the following procedure: Half of the insulin was added to a mixing device comprising a mixing cylinder of volume 4.4 litres divided, by a sieve of width 1 mm, into two compartments, with a metal ring in each compartment to aid mixing and stirring. The sodium caprate and finally the rest of the insulin, were added. The mixing cylinder was closed, turned 180 degrees, and mounted in a motorised shaking apparatus. The motor was turned on and shaking continued for approximately two minutes, until all the insulin and sodium caprate had passed through the sieve. The motor was turned off and the mixing cylinder turned 180 degrees, again mounted on the shaking apparatus and shaking was again effected until all the powder had passed through the sieve. This procedure was repeated a further eight times to give a total mixing time of approximately 20 minutes.

The preparation so obtained was administered to 5 dogs by inhalation, at a dosage level of 1 U./kg, and the plasma insulin level determined at various time points after administration.

The results obtained were compared with the plasma insulin levels obtained when biosynthetic insulin, micronised as above to a mass median diameter of 2.4 micrometers, was administered to five dogs in the same way and at the same dosage levels, and with the plasma insulin levels obtained when a therapeutic preparation of insulin and sodium caprate in a ratio of 90:10 was administered to five dogs in the same way and at the same dosage levels as above. In this case the therapeutic preparation was prepared as follows: Human semisynthetic insulin was gel filtrated to reduce the zinc content from 0.52% to 0.01% relative to content of insulin. Insulin (4.5 g) and sodium caprate (0.5 g) were dissolved in water (232 ml). The solution was stirred until clear and the pH adjusted to 7.0. The solution was concentrated by evaporation at 37° C. over a period of about two days. The obtained solid cake was crushed, and sieved through a 0.5 mm sieve, and the resultant powder micronised through a jet mill to particles with a mass median diameter of 3.1 micrometers.

Figure 10:
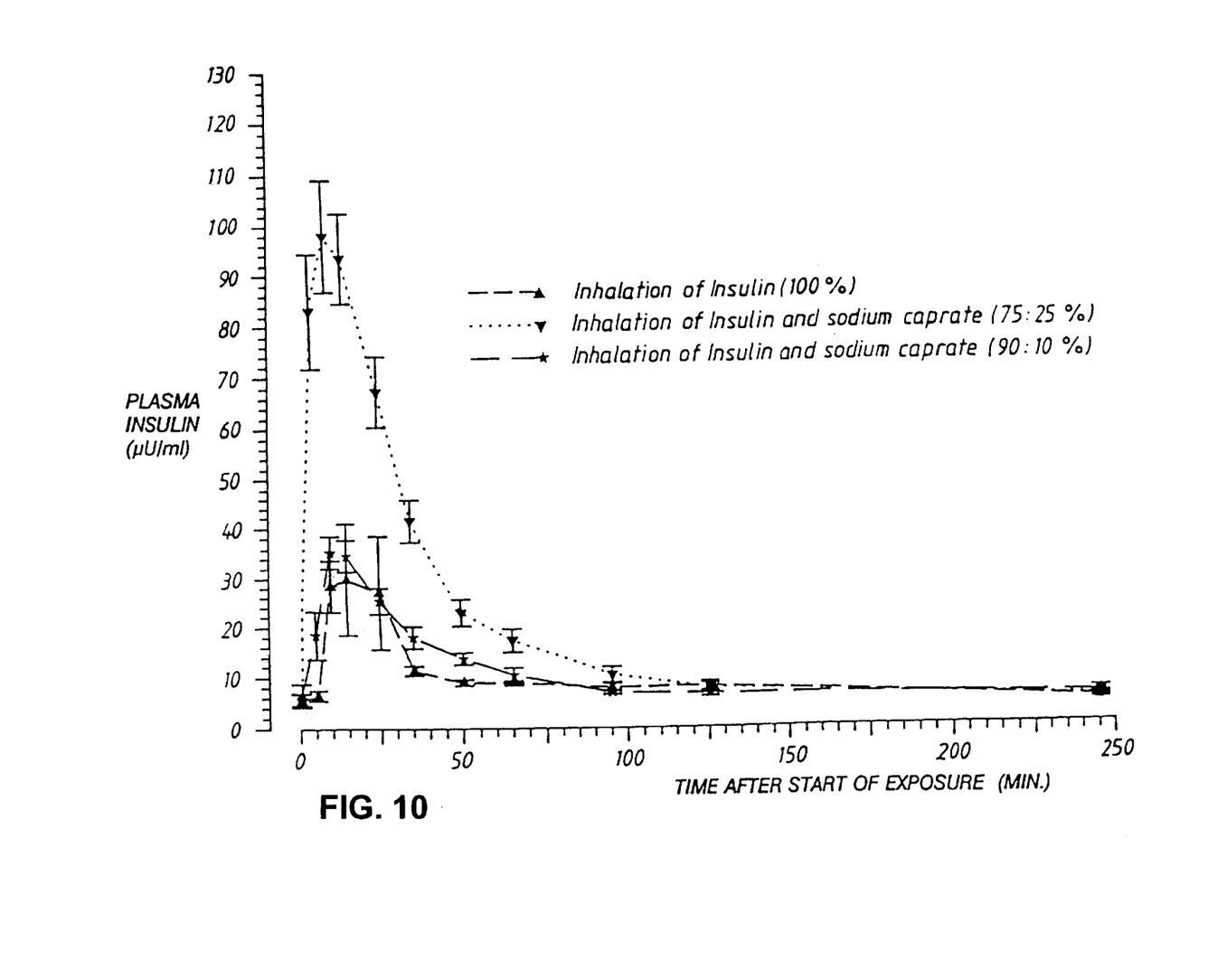
FIG. 10 is a graph of plasma insulin concentration as a function of time after inhalation of insulin alone, insulin with sodium caprate in a ratio of 90:10, and insulin with sodium caprate in a ratio of 75:25.

The results of these comparisons are presented in FIG. 10. The results demonstrate some improvement in the bioavailability of insulin with the 90:10 formulation, and a dramatic improvement in the bioavailablity of insulin with the 75:25 preparation according to the present invention, as compared to insulin alone. (p=0.0147 for the difference between 75:25 and 100:0)

EXAMPLE 5

Each of the compounds listed in Table III was tested for its ability to enhance uptake of insulin, and thus affect blood glucose levels, in a rat model. Various forms of insulin were employed: recombinant or semisynthetic human or bovine. Each formulation was prepared as above, drying and processing the insulin/enhancer or insulin/enhancer/lactose solution to produce an inhalable powder.

The powder was administered to rats by inhalation, and the blood glucose levels of the rats were subsequently monitored. These levels were compared to the corresponding values obtained from rats which had inhaled insulin formulations without enhancer.

TABLE III

| Substance | Enhancer:Insulin:lactose | Effect |
|---|---|---|
| Octylglucopyranoside | 4:4:92 | (+) |
| Sodium ursodeoxycholate | 4:4:92 | + |
| Sodium taurocholate | 4:4:92 | + |
| Sodium glycocholate | 4:4:92 | + |
| Lysophosphatidylcholine | 4:4:92 | + |
| Dioctanoylphosphatidylcholine | 2:4:94 | (+) |
| Didecanoylphospatidylcholine | 4:4:94 | − |
| Sodium taurodihydrofusidate | 2:4:94 | + |
| Sodium caprylate | 25:75:0 | − |
| Sodium caprate | 10:90:0 | (+) |
| Sodium caprate | 17.5:82.5:0 | (+) |
| Sodium caprate | 25:75:0 | + |
| Sodium caprate | 4:4:92 | + |
| Sodium laurate | 25:75:0 | (+) |
| Potassium oleate | 4:4:92 | + |
| Potassium caprate | 27:73:0 | + |
| Lysine caprate | 35:65:0 | + |
| Sodium myristate | 30:70:0 | + |
| Dimethyl-β-cyclodextrin | 75:25:0 | + |

+ significant decrease in blood glucose level
(+) moderate decrease in blood glucose level
− no or very small decrease in blood glucose level

EXAMPLE 6

Figure 6:
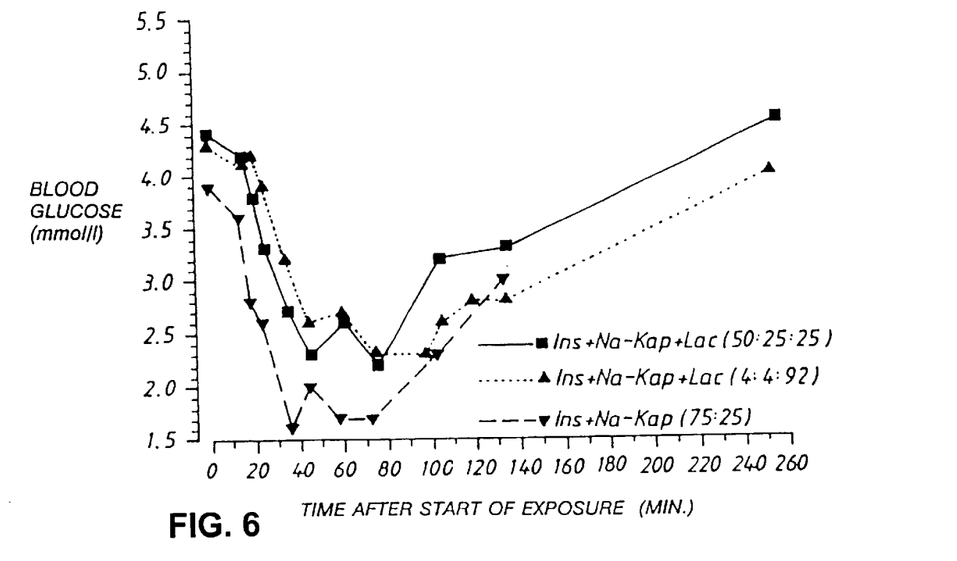
FIG. 6 is a graph illustrating the effect of inhaling each of three different insulin/sodium caprate formulations on blood glucose levels in the experiment referred to in FIG. 2.
Figure 7:
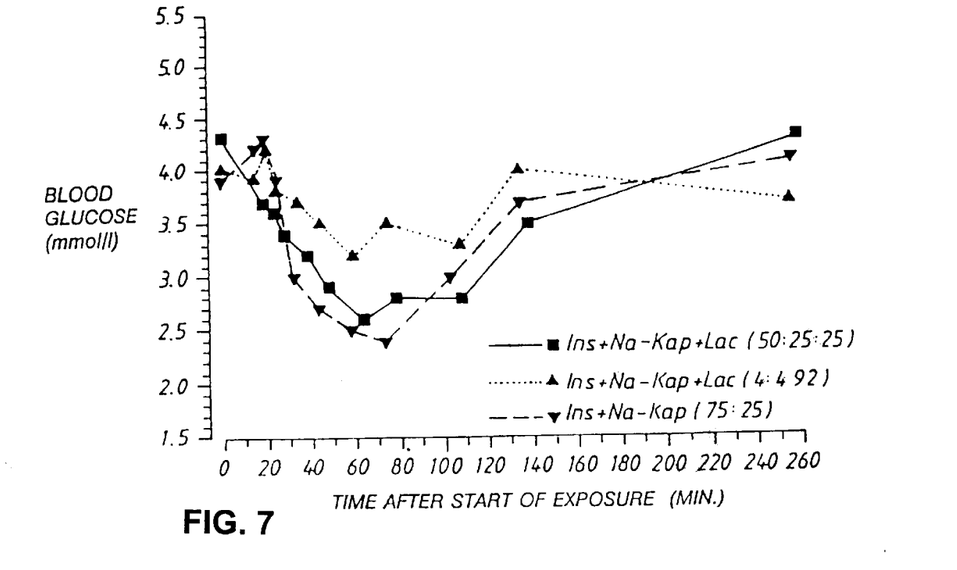
FIG. 7 is a graph illustrating the effects of inhaling each of three different insulin/sodium caprate formulations on blood glucose levels in the experiment referred to in FIG. 3.
Figure 8:
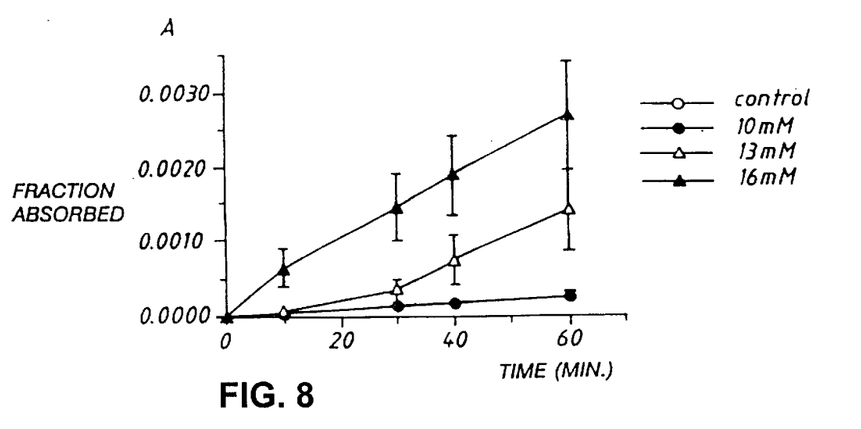
FIG. 8 is a graph showing that the amount of absorption of a labelled marker, mannitol, across an epithelial cell monolayer in vitro is dependent upon the concentration of enhancer (sodium caprate) used.
Figure 9:
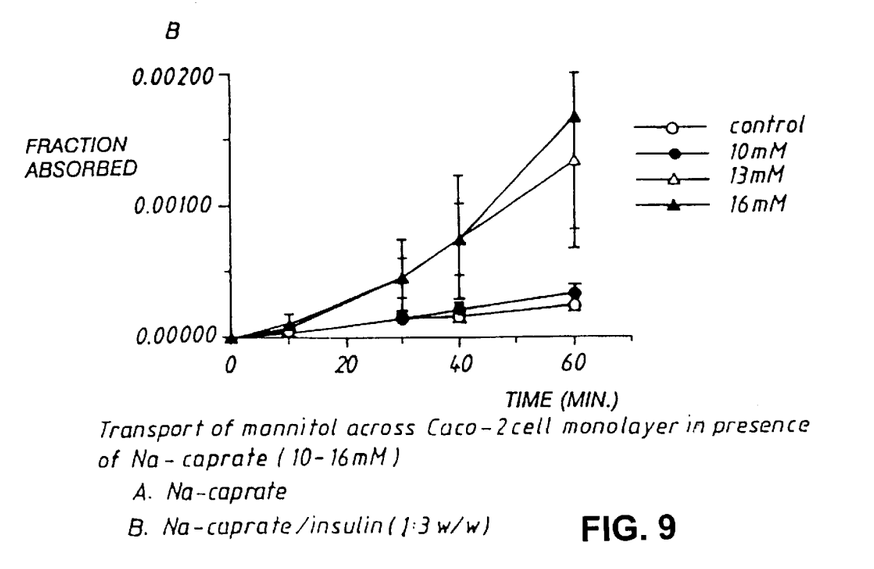
FIG. 9 is a graph of an experiment as in FIG. 6., except that insulin is also present in the mannitol/enhancer mixture.

A standard in vitro assay utilizing an epithelial cell line, CaCo-2 (available through the American Type Culture Collection (ATCC), Rockville, Md., USA), has been developed to assess the ability of various enhancer compounds to promote transport of insulin and other markers across an epithelial cell monolayer, as a model for the epithelial cell layer which functions in the lung to separate the alveolus from the pulmonary blood supply. In this assay, the enhancer and insulin or other marker are dissolved in aqueous solution at various proportions and/or concentrations, and applied to the apical side of the cell monolayer. After 60 min incubation at 37° C. and 95% RH (relative humidity), the amount of the marker on the basolateral side of the cells is determined: for example, by use of a radioactively labelled marker. For the particular enhancer (sodium caprate) tested in the experiments shown in FIGS. 6 and 7, the amount of marker (mannitol, MW 360) which appears on the basolateral side is dependent upon the concentration of enhancer used, at least up to 16 mM sodium caprate (FIG. 8). This is true even when insulin is added to the enhancer/mannitol mixture (1:3 sodium caprate:insulin, by weight) (FIG. 9). This concentration of sodium caprate (16 mM) was also found to promote absorption of insulin across the cell monolayer. The amount of insulin which passed across the monolayer doubled in the presence of 16 mM sodium caprate, compared to the amount in the absence of any enhancer. It is expected that at higher concentrations of sodium caprate, the permeability of the cells will be further increased; however, the potential cytotoxicity of sodium caprate may prevent the use of substantially higher concentrations of this particular enhancer.

This in vitro model of epithelial cell permeability can be used as a screening tool for rapidly testing any desired enhancer for usefulness in the methods of the invention.

What is claimed is:
1. A method of treating a patient in need of insulin treatment, comprising introducing through the mouth and into the lower respiratory tract of said patient an effective amount of a dry powder composition, the active ingredients of which consist of (a) insulin and (b) one or more enhancers which enhance the absorption of insulin in the lower respiratory tract of said patient, each of the one or more enhancers being selected from the group consisting of a bile salt, a $C_8$–$C_{16}$ fatty acid, a salt of a $C_8$–$C_{16}$ fatty acid, an acyl carnitine, a salt of glycyrrhizine, a phospholipid, a cyclodextrin, and an alkyl saccharide, wherein the dry powder composition is introduced into the lower respiratory tract of the patient by inhalation from a dry powder inhaler device, provided that, if any of the one or more enhancers is a double-chain phospholipid, each chain of the double-chain phospholipid is eight or fewer carbon atoms in length.

2. The method of claim 1, wherein at least 50% of the total mass of said active ingredients in said dry powder composition, at the point of introduction into the respiratory system of said patient, consists of particles having a diameter of about 10 microns or less.

3. The method of claim 2, wherein said dry powder composition is supplied as agglomerates of said particles of said active ingredients contained in an inhaler device, said agglomerates being substantially deagglomerated prior to entry into the respiratory system of said patient.

4. The method of claim 3, wherein the dry powder composition is supplied as an ordered mixture of particles of active ingredients having a diameter of about 10 microns or less and particles of a carrier substance additionally comprised in said dry powder composition, contained in an inhaler device.

5. The method of claim 3, wherein said particles are inhaled by said patient from said inhaler device, said agglomerates being substantially deagglomerated by air turbulence in said inhaler device.

6. The method of claim 2, wherein said patient inhales said dry powder composition from a single-dose, dry powder inhaler device.

7. The method of claim 1, wherein said insulin is human insulin.

8. The method of claim 1, wherein said one or more enhancers includes a trihydroxy bile salt.

9. The method of claim 1, wherein said one or more enhancers includes a salt of cholic, glycocholic, or taurocholic acid.

10. The method of claim 1, wherein said one or more enhancers includes a sodium or potassium salt of cholic acid.

11. The method of claim 1, wherein said one or more enhancers includes a sodium or potassium salt of glycocholic acid.

12. The method of claim 1, wherein said one or more enhancers includes sodium taurocholate.

13. The method of claim 1, wherein said one or more enhancers includes potassium taurocholate.

14. The method of claim 1, wherein said one or more enhancers includes a salt of chenodeoxycholic acid, glycochenodeoxycholic acid, taurochenodeoxycholic acid, deoxycholic acid, glycodeoxycholic acid, taurodeoxycholic acid, lithocholic acid, or ursodeoxycholic acid.

15. The method of claim 1, wherein the ratio of (a) to (b) in said dry powder composition is between about 9:1 and about 1:1.

16. The method of claim 1, wherein at least 50% of the total mass of said active ingredients is in the form of particles which have a diameter of 10 microns or less, or of agglomerates of said particles.

17. A method of treating a patient in need of insulin treatment, comprising introducing into the lower respiratory tract of the patient, from a dry powder inhaler device, a dry powder pharmaceutical preparation, the active ingredients of which consist of (a) insulin and (b) one or more enhancers which enhance the systemic absorption of insulin in the lower respiratory tract of said patient, each of the one or more enhancers being selected from the group consisting of a bile salt, a $C_8$–$C_{16}$ fatty acid, a salt of a $C_8$–$C_{16}$ fatty acid, an acyl carnitine, a salt of qlycyrrhizine, a phospholipid, a cyclodextrin, and an alkyl saccharide, provided that, at the point the preparation enters the respiratory tract of the patient, at least 50% of the total mass of active ingredients consists of particles having a diameter of about 10 microns or less, wherein the plasma pharmacokinetics of said insulin delivered by said method more closely resemble the plasma pharmacokinetics of endogenous insulin secreted by a healthy individual in response to a glucose challenge, than do the plasma pharmacokinetics of human insulin delivered by subcutaneous injection.

18. The method of claim 17, wherein said one or more enhancers includes a trihydroxy bile salt.

19. The method of claim 17, wherein said one or more enhancers includes a salt of cholic, glycocholic, or taurocholic acid.

20. The method of claim 17, wherein said one or more enhancers includes a sodium or potassium salt of cholic acid.

21. The method of claim 17, wherein said one or more enhancers includes a sodium or potassium salt of glycocholic acid.

22. The method of claim 17, wherein said one or more enhancers includes sodium taurocholate.

23. The method of claim 17, wherein said one or more enhancers includes potassium taurocholate.

24. The method of claim 17, wherein said one or more enhancers includes a salt of chenodeoxycholic acid, glycochenodeoxycholic acid, taurochenodeoxycholic acid, deoxycholic acid, glycodeoxycholic acid, taurodeoxycholic acid, lithocholic acid, or ursodeoxycholic acid.

25. The method of claim 17, wherein the ratio of (a) to (b) in said dry powder pharmaceutical preparation is between about 9:1 and about 1:1.

26. The method of claim 17, wherein said patient inhales said dry powder pharmaceutical preparation from a single-dose, dry powder inhaler device.

27. The method of claim 1, wherein the dry powder composition contains only said active ingredients.

28. The method of claim 1, wherein the dry powder composition contains, in addition to said active ingredients, a pharmaceutically acceptable carrier.

29. The method of claim 1, wherein said one or more enhancers includes a sodium, potassium or lysine salt of caprylic acid ($C_8$), capric acid ($C_{10}$), lauric acid ($C_{12}$), or myristic acid ($C_{14}$).

30. The method of claim 1, wherein said one or more enhancers includes a single- or double-chain phospholipid.

31. The method of claim 1, wherein said one or more enhancers includes at least one phospholipid selected from the group consisting of lysophosphatidylcholine, lysophosphatidylglycerol, lysophosphatidylethanolamine, lysophosphatidylinositol, lysophosphatidylserine, diacylphosphatidylcholine, diacylphosphatidylglycerol, diacylphosphatidylethanolamine, diacylphosphatidylinositol, and diacylphosphatidylserine.

32. The method of claim 1, wherein said one or more enhancers includes palmitoylphosphatidylglycerol, palmitoylphosphatidylcholine, dioctanoylphosphatidylglycerol or dioctanoylphosphatidylcholine.

33. The method of claim 1, wherein said one or more enhancers includes an alkyl glucoside or alkyl maltoside.

34. The method of claim 1, wherein said one or more enhancers includes decyl glucoside, dodecyl glucoside, decyl maltoside, or dodecyl maltoside.

35. The method of claim 1, wherein said one or more enhancers includes a sodium or potassium salt of glycyrrhizine.

36. The method of claim 1, wherein said one or more enhancers includes decanoyl carnitine, lauryl carnitine, myristoyl carnitine, or palmitoyl carnitine.

37. The method of claim 1, in which at least 50% of the dry powder composition consists of (a) particles having a diameter of between 1 and 6 microns or (b) agglomerates of such particles.

* * * * *